ID Bertin et al.

[11] 4,425,351
[45] Jan. 10, 1984

[54] THERAPEUTICALLY USEFUL OXYGEN DERIVATIVES OF 3,7A-DIAZACYCLOHEPTA[J,K]FLUORENES

[75] Inventors: Jean Bertin, Clamart; Jonathan R. Frost, Cachan, both of France

[73] Assignee: Synthelabo, Paris, France

[21] Appl. No.: 446,358

[22] Filed: Dec. 2, 1982

[30] Foreign Application Priority Data

Dec. 3, 1981 [FR] France ................................ 81 22642

[51] Int. Cl.³ ..................... A61K 31/55; C07D 471/14
[52] U.S. Cl. ............................. 424/262; 260/239.3 P
[58] Field of Search .................. 260/239.3 P; 424/262

[56] References Cited

U.S. PATENT DOCUMENTS 4,228,168 10/1980 Sato et al. ..................... 260/239.3 P

FOREIGN PATENT DOCUMENTS 816756 10/1974 Belgium ........................ 260/239.3 P
882024  9/1980 Belgium ........................ 260/239.3 P
56-161383 12/1981 Japan .......................... 260/239.3 P

OTHER PUBLICATIONS

Lazarone et al., "Bull. Soc. Chim. France", (1977), Nos. 11–12, pp. 1207–1214.

Primary Examiner—Robert T. Bond
Attorney, Agent, or Firm—Wegner & Bretschneider

[57] ABSTRACT

Compounds of the general formula:

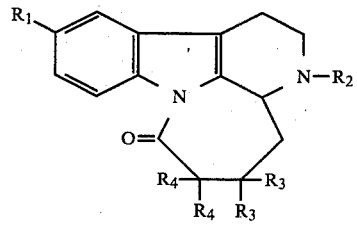

wherein $R_1$ represents hydrogen, chlorine or methoxy, $R_2$ represents hydrogen, methyl or benzyl, and $R_3$ and $R_4$ represent hydrogen, or $R_3$ represents methyl and $R_4$ represents hydrogen, or $R_3$ represents hydrogen and $R_4$ represents methyl, with the exception of those compounds wherein $R_1$, $R_3$ and $R_4$ each represent a hydrogen atom simultaneously, are new therapeutically useful compounds; they possess an antianoxic activity.

8 Claims, No Drawings

THERAPEUTICALLY USEFUL OXYGEN DERIVATIVES OF 3,7A-DIAZACYCLOHEPTA[J,K]FLUORENES

DESCRIPTION

The present invention relates to new therapeutically useful oxygen derivatives of 3,7a-diazacyclohepta[j,k]-fluorenes, to their preparation and pharmaceutical compositions containing them.

The compounds of the present invention correspond to the general formula:

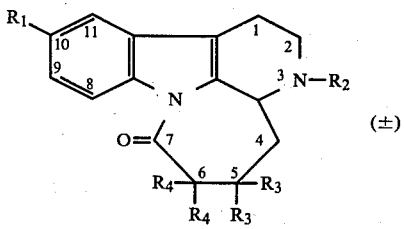

(I)

wherein $R_1$ represents a hydrogen or chlorine atom or a methoxy radical, $R_2$ represents a hydrogen atom or the methyl or benzyl radical, and $R_3$ and $R_4$ represent hydrogen atoms, or $R_3$ represents the methyl radical and $R_4$ represents a hydrogen atom, or $R_3$ represents a hydrogen atom and $R_4$ represents the methyl radical, with the exception of those compounds wherein $R_1$, $R_3$ and $R_4$ each represent a hydrogen atom simultaneously, and pharmacologically-acceptable acid addition salts thereof.

Compounds of general formula (I) wherein $R_1$, $R_3$ and $R_4$ each represent a hydrogen atom are described in French Pat. No. 2442236.

The compounds of general formula (I) can exist in the form of racemates or enantiomers, and all such forms are part of the invention.

According to a feature of the invention, the compounds of general formula(I) wherein $R_2$ represents the methyl or benzyl radical are prepared according to the following reaction scheme:

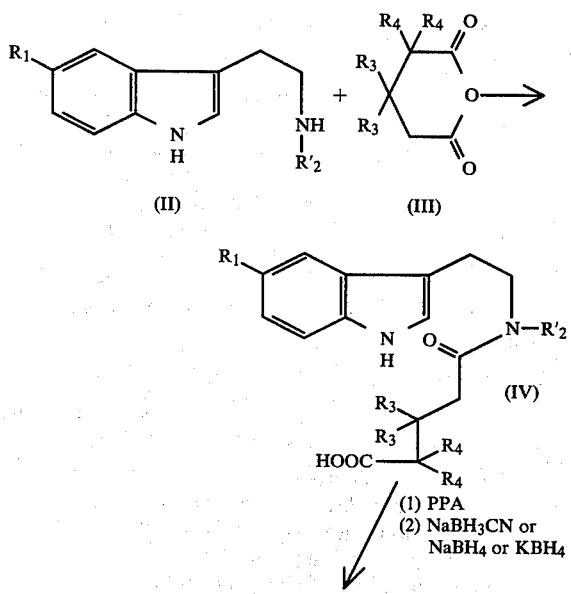

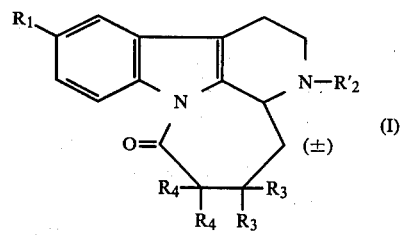

wherein $R'_2$ represents the methyl or benzyl radical, and the symbols $R_1$, $R_3$ and $R_4$ are as hereinbefore defined.

A tryptamine (II) wherein $R'_2$ represents the methyl or benzyl radical is reacted with a compound (III) in an organic solvent, for example benzene, at the reflux temperature; the compound (IV) is then reacted, under the action of heat, with polyphosphoric acid (abbreviated to PPA) and then with sodium cyanoborohydride, sodium borohydride or potassium borohydride; this gives a compound (I) in which $R'_2$ is the methyl or benzyl radical.

To obtain a compound (I) wherein $R_2$ represents a hydrogen atom the corresponding compound (I) wherein $R'_2$ is the benzyl radical is debenzylated by catalytic hydrogenation.

Pharmacologically-acceptable acid addition salts of the compounds of general formula (I) can be obtained by methods known per se, for example by reacting the basic compound with an acid, the anion of which is relatively innocuous to the animal organism in therapeutic doses of the salts, e.g. hydrochloric, methanesulphonic, fumaric or maleic acid.

The Examples which follow illustrate the preparation of compounds of the invention.

The analyses and the IR and NMR spectra confirm the structure of the compounds.

EXAMPLE 1

3-Benzyl-5,5-dimethyl-7-oxo-1,2,3,3a,4,5,6,7-octahydro-3,7a-diazacyclohepta[j,k]fluorene

1.

3-[2-(N-(4-carboxy-3,3-dimethyl-1-oxobutyl)-N-benzylamino)-ethyl]-indole 28.6 g of 3-(2-benzylaminoethyl)-indole and 150 ml of concentrated sodium hydroxide solution are introduced into a 500 ml Erlenmeyer flask provided with a magnetic stirrer. The mixture is stirred at ambient temperature for a few minutes, 200 ml of ethyl acetate are then added and the mixture is stirred at ambient temperature for 30 minutes. The organic phase is decanted, the aqueous phase is taken up in ethyl acetate, and the organic phases are combined, dried over MgSO₄ and concentrated. This gives an oil, which is the starting base (II).

25.1 g of the base obtained as described above, in 200 ml of benzene, and then 14.25 g of 3,3-dimethylglutaric anhydride are introduced into a 1 liter round-bottomed flask provided with a condenser, a CaCl₂ drying tube and a magnetic stirrer. The reaction mixture is heated at the reflux temperature for 2 hours 30 minutes, using an oil bath. It is then left to stand at ambient temperature overnight, then concentrated, and the compound is crystallised by adding 150 ml of diisopropyl ether and stirring. The product is filtered off and dried. Its melting point is 124° C.

2.

3-Benzyl-5,5-dimethyl-7-oxo-1,2,3,3a,4,5,6,7-octahydro-3,7a-diazacyclohepta[j,k]fluorene and its maleate

8.95 g of the crude product obtained as described above and 65.7 g of polyphosphoric acid are introduced into a 500 ml round-bottomed flask. The flask is immersed in an oil bath at 90° C., the mixture is stirred for 2 hours 30 minutes and then cooled. This is followed by the addition of 100 ml of water and 5 N sodium hydroxide solution to pH 4 to 5 and then by the rapid addition of 4.6 g of NaBH$_3$CN.

The reaction mixture is stirred at ambient temperature for 1 hour. It is left to stand overnight at ambient temperature. 20 ml of concentrated hydrochloric acid are added and the reaction mixture is heated at the reflux temperature for 1 hour. After cooling, it is rendered alkaline with 5 N sodium hydroxide solution and then extracted twice with ethyl acetate (400 ml). The extracts are dried over MgSO$_4$ and concentrated. The concentrate is chromatographed on 230 g of silica and elution is carried out with CH$_2$Cl$_2$. The base thus obtained is used to prepare the maleate in ethyl acetate. Recrystallized from isopropyl alcohol, the maleate melts at 176°–178° C.

EXAMPLE 2

3-Methyl-6,6-dimethyl-7-oxo-1,2,3,3a,4,5,6,7-octahydro-3,7a-diazacyclohepta[j,k]fluorene

1.

3-[2-(N-(4-carboxy-4,4-dimethyl-1-oxobutyl)-N-methylamino)-ethyl]-indole

6.97 g of 3-(2-methylaminoethyl)-indole, 100 ml of dry benzene and 5.69 g of 2,2-dimethylglutaric anhydride are introduced at ambient temperature into a 250 ml round-bottomed flask provided with a condenser, a CaCl$_2$ drying tube and a magnetic stirrer. The reaction mixture is heated slowly at the reflux temperature for 1 hour 30 minutes with stirring. It is then left to cool and to stand overnight at ambient temperature.

The crystals formed are filtered off, washed with benzene, dried and recrystallised from ethyl acetate. The melting point of the compound obtained is 135° C.

2.

3-Methyl-6,6-dimethyl-7-oxo-1,2,3,3a,4,5,6,7-octahydro-3,7a-diazacyclohepta[j,k]fluorene

320 g of polyphosphoric acid and 32 g of the compound obtained as described above are introduced into a 2 liter reactor provided with a mechanical stirrer.

The round-bottomed flask is immersed in an oil bath at 90° C. and the reaction mixture is then stirred for 3 hours 30 minutes. After cooling in an ice bath, 200 ml of water are added, followed by 5 N sodium hydroxide solution to pH 5. 32 g of NaBH$_3$CN are then added rapidly and the mixture is stirred for 1 hour at ambient temperature. 20 ml of concentrated hydrochloric acid are added slowly, the mixture is stirred for a few minutes and 500 ml of ethyl acetate are then added.

The reaction mixture is stirred and then left to stand overnight at ambient temperature. It is rendered basic with 5 N sodium hydroxide solution, the organic phase is then decanted, the aqueous phase is taken up in ethyl acetate, and the organic phases are combined, dried over MgSO$_4$ and concentrated.

After chromatography on silica and elution with CH$_2$Cl$_2$, an oil is obtained.

EXAMPLE 3

5,5-Dimethyl-7-oxo-1,2,3,3a,4,5,6,7-octahydro-3,7a-diazacyclohepta[j,i]fluorene and its maleate

1 g of the product (base) prepared according to Example 1 is placed in a Parr flask together with 25 ml of ethanol, 2.5 ml of acetic acid and 0.1 g of 10% palladium-on-charcoal. The suspension is stirred, a hydrogen pressure of about 0.35 Mpa is established and the stirring is continued for 2 hours 30 minutes at ambient temperature. Thin layer chromatography shows that the reaction is complete. A few drops of chloroform are then added to the mixture in order to deactivate the catalyst, the mixture is filtered in order to remove the latter, and the filtrate is concentrated. Water is added, followed by dilute ammonia solution to pH 10. The mixture is extracted twice with ethyl acetate, and the organic phase is dried over magnesium sulphate and then concentrated in vacuo. This gives white crystals of the title product.

The maleate, which is obtained by adding maleic acid to a solution of the base (in ethyl acetate), is recrystallised from isopropyl alcohol. It melts at 224° C.

EXAMPLE 4

3-Benzyl-10-chloro-7-oxo-1,2,3,3a,4,5,6,7-octahydro-3,7a-diazacyclohepta[j,k]fluorene

1.

3-[2-(N-(4-carboxy-1-oxobutyl)-N-benzylamino)-ethyl]-indole

113 g (0.396 mol) of 3-(2-benzylaminoethyl)-5-chloroindole are dissolved in 500 ml of benzene. 45.27 g of glutaric anhydride are added in small amounts and the reaction mixture is heated at the reflux temperature for 2 hours and then left to stand overnight. It is evaporated to dryness. This gives the named product.

2.

3-Benzyl-10-chloro-7-oxo-1,2,3,3a,4,5,6,7-octahydro3,-7a-diazacyclohepta[j,k]fluorene and its methanesulphonate

A mixture of 20 g of the compound obtained as described above and 200 g of polyphosphoric acid is heated at 90° C. for 2 hours and 30 minutes. The reaction mixture is cooled and ice and water are added. Sodium hydroxide solution is then added to pH 4.5, followed by 18.8 g of NaBH$_3$CN. The reaction mixture is stirred for 1 hour 30 minutes. It is then cooled and sodium hydroxide solution is added to pH 7.5. The product is extracted with ethyl acetate, and the extract is dried over MgSO$_4$ and evaporated to dryness.

After chromatography on silica and elution with a 99/1 chloroform/acetone mixture, the product is obtained in the form of the base.

The methanesulphonate of the base is prepared in ethanol. The salt is recrystallised from absolute alcohol. Its melting point is 184° C.

EXAMPLE 5

10-Chloro-7-oxo-1,2,3,3a,4,5,6,7-octahydro-3,7a-diazacyclohepta[j,k]fluorene and its hydrochloride

3.6 g of the compound (base) obtained according to Example 4 are dissolved in 100 ml of acetic acid, and debenzylation with hydrogen is carried out at ambient temperature, under a pressure of about 0.35 Mpa, in the presence of 0.36 g of platinum oxide. A whitish precipitate is formed, which is dissolved by adding distilled water. The catalyst is removed by filtration and the mixture is evaporated to dryness. The residual semi-crystalline oil is taken up in water containing ammonia, and the base freed in this way is extracted with ethyl acetate. The organic phases are combined, washed with water, dried over magnesium sulphate and evaporated to dryness. The oil obtained is chromatographed with an 80/20 mixture of chloroform and methanol. The base obtained is dissolved in ethanol, and the pure hydrochloride is precipitated by adding a 2.5 N solution of hydrogen chloride in diethyl ether. The hydrochloride is isolated and recrystallised from methanol. It does not melt below 300° C.

By converting the hydrochloride back to the base and chromatographing the latter on silica with a 90/10 mixture of chloroform and methanol, a pure oil is collected, which crystallises from pentane. Its melting point is 136°–138° C.

The following Table by reference to general formula (I) illustrates other compounds according to the invention obtained by analogous methods.

TABLE (I)

| Compound | $R_1$ | $R_2$ | $R_3$ | $R_4$ | form | Melting point (°C.) |
|---|---|---|---|---|---|---|
| 1 | H | $C_6H_5CH_2$ | $CH_3$ | H | HCCOOH ‖ HCCOOH | 176–8 |
| 2 | H | $CH_3$ | H | $CH_3$ | base | oil |
| 3 | H | H | $CH_3$ | H | HCCOOH ‖ HCCOOH | 224 |
| 4 | Cl | $C_6H_5CH_2$ | H | H | $CH_3SO_3H$ | 184 |
| 5 | Cl | H | H | H | base HCl | 136–8 >300 |
| 6 | H | $CH_3$ | $CH_3$ | H | HCCOOH ‖ HCCOOH | 178–80 |
| 7 | H | H | H | $CH_3$ | HCCOOH ‖ HCCOOH | 205 |
| 8 | $CH_3O$ | $C_6H_5CH_2$ | H | H | base HCl | 132–4 226–8 |
| 9 | H | $C_6H_5CH_2$ | H | $CH_3$ | HCCOOH ‖ HCCOOH | 164–5 |

The compounds of the invention were subjected to pharmacological tests for the purpose of demonstrating their value in therapy.

Acute toxicity to mice

The compounds are administered to the test animals in increasing doses. The toxicity of the compounds is expressed by the dose, in mg per kg of body weight, at which half of the animals in the batch corresponding to each test survive. It is thus found that, by intraperitoneal administration, the $LD_{50}$ values of the compounds range from 30 mg/kg to 600 mg/kg whereas, by oral administration, they range from 300 mg/kg to more than 1000 mg/kg.

Antianoxic activity

When administered intraperiteoneally, the compounds of the invention prolong the life of mice placed in an oxygen-depleted atmosphere (produced by creating a partial vacuum in a closed chamber in which the pressure is brought to $2.5 \times 10^4$ Pa (190 mm Hg) in 30 seconds using a vacuum pump).

The activity of the compounds is expressed by the $AD_{100}$, that is to say the dose in mg/kg animal body weight which prolongs the survival time of the treated animals by 100%, compared with the survival time of the contraol animals.

The $AD_{100}$ values of the compounds of the invention are between 5 and 30 mg/kg.

Total ischaemia test in mice

The survival time of the test animals is measured after they have been injected in the caudal vein with 0.1 ml of a saturated solution of magnesium chloride. The cardiac arrest which results causes cerebral ischaemia. The "survival time" is the period of time between the injection of the magnesium chloride and the last inspiratory movement of each mouse, which is considered as the final indication of function of the central nervous system.

The survival times of the animals treated with the compounds of the invention, administered intraperitoneally 10 minutes before the injection of the magnesium chloride, are compared with the survival times of the control animals, to which only the vehicle for the active substances has been administered.

The mice are studied in groups of 10 and the averages of the results of each group make it possible to plot a curve; this permits a graphical determination of the Effective Dose 3, $ED_3$, expressed in mg of active substance per kg of body weight, which prolongs the survival time by 3 seconds.

An increase in 3 seconds in the survival time is both statistically significant and reproducible.

The $ED_3$ values of the compounds of the invention range from 3 to 60 mg/kg.

The pharmacological study of the compounds of the invention shows that they possess an antianoxic activity and that they can be used in therapy for the treatment of vigilance disorders, in particular for combating the behavioural disorders attributable to cerebral vascular damage and to the cerebral sclerosis encountered in geriatrics, and also for the treatment of the absences due to cranial traumatisms, for the treatment of metabolic encephalopathies and for the treament of depressive states.

The invention consequently includes all pharmaceutical compositions containing the compounds of the invention or their salts as active principles, in association with any excipients which are suitable for their administration, in particular their oral or parenteral administration.

The daily dosage can range from 1 to 100 mg, administered parenterally, and from 5 to 500 mg, administered orally, the dose units containing, for example, 1 to 100 mg doses of active substance.

We claim:

1. A compound of the formula:

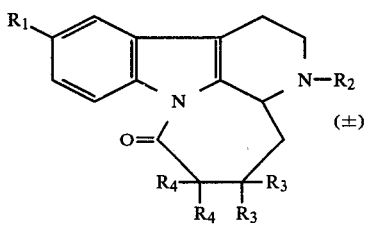

wherein $R_1$ represents a hydrogen or chlorine atom or a methoxy radical, $R_2$ represents a hydrogen atom or the methyl or benzyl radical, and $R_3$ and $R_4$ represent hydrogen atoms, or $R_3$ represents the methyl radical and $R_4$ represents a hydrogen atom, or $R_3$ represents a hydrogen atom and $R_4$ represents the methyl radical, excluding such a compound wherein $R_1$, $R_3$ and $R_4$ each represent a hydrogen atom simultaneously, and its pharmacologically-acceptable acid addition salts.

2. A compound according to claim 1 which is 3-benzyl-5,5-dimethyl-7-oxo-1,2,3,3a,4,5,6,7-octahydro-3,7a-diazacyclohepta[j,k]fluorene and its pharmacologically-acceptable acid addition salts.

3. A compound according to claim 1 which is 3-methyl-6,6-dimethyl-7-oxo-1,2,3,3a,4,5,6,7-octahydro-3,7a-diazacyclohepta[j,k]fluorene and its pharmacologically-acceptable acid addition salts.

4. A compound according to claim 1 which is 5,5-dimethyl-7-oxo-1,2,3,3a,4,5,6,7-octahydro-3,7a-diazacyclohepta[j,k]fluorene and its pharmacologically-acceptable acid addition salts.

5. A compound according to claim 1 which is 3-benzyl-10-chloro-7-oxo-1,2,3,3a,4,5,6,7-octahydro-3,7a-diazacyclohepta[j,k]fluorene and its pharmacologically-acceptable acid addition salts.

6. A compound according to claim 1 which is 10-chloro-7-oxo-1,2,3,3a,4,5,6,7-octahydro-3,7a-diazacyclohepta[j,k]fluorene and its pharmacologically-acceptable acid addition salts.

7. A pharmaceutical composition which comprises a compound as claimed in claim 1, or a pharmacologically-acceptable acid addition salt thereof, in association with a pharmaceutically-acceptable excipient.

8. A method for the treatment of vigilance disorders, in particular, for combating the behavioural disorders attributable to cerebral vascular damage or to the cerebral sclerosis encountered in geriatrics, or for the treatment of absences due to cranial traumatisms, for the treatment of metabolic encephalopathies and for the treatment of depressive states, which comprises administering to a patient with such an ailment an amount of a compound of the formula specified in claim 1, or a pharmacologically-acceptable acid addition salt thereof, effective to ameliorate the condition of the patient.

* * * * *